United States Patent [19]

Ellingsen

[11] Patent Number: 4,923,457
[45] Date of Patent: May 8, 1990

[54] ARTIFICIAL GLAND FOR IMPLANTATION IN A HUMAN BODY

[75] Inventor: Olav Ellingsen, Florø, Norway

[73] Assignee: Industrikontakt Ing. O. Ellingsen & Co., Florø, Norway

[21] Appl. No.: 933,755

[22] Filed: Nov. 21, 1986

[30] Foreign Application Priority Data

Nov. 22, 1985 [NO] Norway .................................. 854668

[51] Int. Cl.$^5$ ........................ A61K 9/22; A61M 11/00; A61F 2/02; A61F 2/04
[52] U.S. Cl. .............................. 604/891.1; 604/892.1; 604/93; 623/11; 623/12
[58] Field of Search ................ 623/11, 12; 604/891.1, 604/892.1, 93, 175

[56] References Cited

U.S. PATENT DOCUMENTS

| | | | |
|---|---|---|---|
| 4,073,292 | 2/1978 | Edelman | 604/66 X |
| 4,309,776 | 1/1982 | Berguer | 623/11 X |
| 4,402,694 | 9/1983 | Ash et al. | 623/12 |

FOREIGN PATENT DOCUMENTS 2195461  3/1974  France .

Primary Examiner—Ronald L. Frinks
Attorney, Agent, or Firm—Ladas & Parry

[57] ABSTRACT

An artificial gland for implantation in the human body and comprising a medicament reservoir intended for being filled with a medicament solution by the aid of a syringe said reservoir, via a passage, being connected with a casing the wall of which casing is completely or partly comprised of a semipermeable membrane that causes changes of pressure by osmosis for delivery of a medicament.

2 Claims, 1 Drawing Sheet

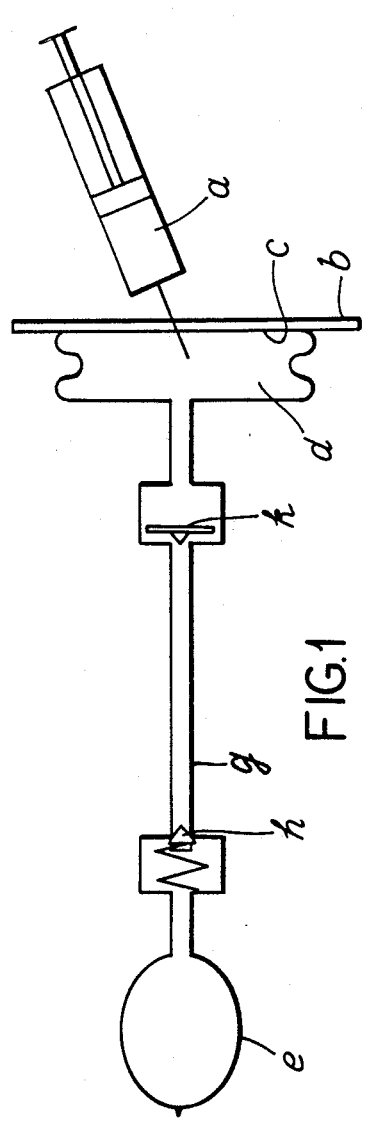
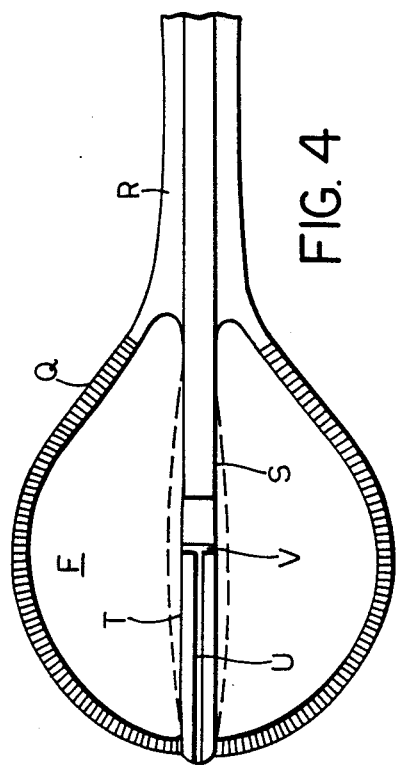
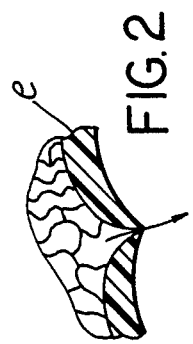
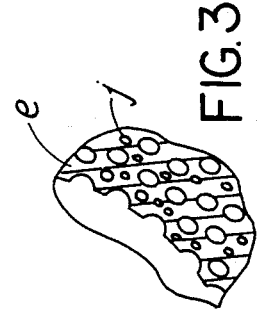
FIG.1
FIG.2
FIG.3
FIG.4

ARTIFICIAL GLAND FOR IMPLANTATION IN A HUMAN BODY

The present invention relates to an artificial gland, e.g. an artificial pancreas, for implantation in the body of a patient suffering from a disease that may be treated/kept in check by continuous administration of a medication as a function of changes of the composition of the patient's blood. As an example of such a disease, we may mention diabetes.

Today, diabetes mellitus is controlled by administration of insulin to a body so diseased by injections. This means that a patient suffering from this disease can keep it in check. If the total amount of insulin necessary for one day is injected in one or two doses, however, considerable disadvantages arise. The patient has to keep a strict diet, which has to be taken at regular intervals during the day, usually at intervals of 3 hours, to keep the blood sugar within acceptable levels. Since the body's consumption of blood sugar is influenced by several factors, however, it may happen, nevertheless, that the blood sugar gets too low, resulting in a so called "feeling". If this state is too heavy or too long-lasting, it may cause brain damage. If the blood sugar gets too high, instead, the same symptoms as with incurable diabetes reoccur, and these may be fatal if left to develop. Furthermore, the so called "late effects" of diabetes are serious problems. Among others, they comprise danger of blindness, problems with veins, etc. A patient suffering from diabetes is also far more vulnerable to infectious diseases than healthy people.

In order to remedy these circumstances, extensive research is being done, both as regards this and diseases making the patient dependent on medicaments. In this connection, so called "insulin pumps" were developed. A patient may adhere such a pump to his body for receiving a supply of insulin through a cannula uniformly all day long. Before a meal, the amount of insulin may also be increased by activating the pump. An implantable pump was also developed, which functions along the same principles, but is filled with a syringe, approximately once a week, through the skin and a membrane of the pump. Activation of said pump before a meal may be achieved, too, with an ultrasonic transmitter. All these pumps resulted in considerable improvement in administering insulin to patients and the general state of their health.

The pumps mentioned, however, are nothing but large syringes containing insulin for several day's consumption. They are not controlled in dependence of the momentary blood sugar level, which is the factor determining the demand for insulin. Furthermore, they have great practical disadvantages. Pumps secured to the outside of an active person's body are exposed to blows, to being torn off, etc., and careful maintenance is needed. Also, the cannula into the human body must be replaced sometimes. The above mentioned implantable pump does not show these disadvantages, but it needs a battery for drive energy, which involves a surgical intervention whenever the battery has to be replaced.

Other implantable medicament pump devices are known from U.S. Pat. Nos. 4 073 292 and 3 923 060.

The first discloses an implantable pancreas for controlling insulin administration as a function of the content of sugar in urine. The detection of changes of the sugar level in the urine is photoelectric, by detection of the passage of light through filtered urine and Benedict's solution. This has the disadvantage that two fluids have to be fed to the body; the medicament, i.e. insulin in the present case, and an activator liquid for the urine, i.e. Benedict's solution in the present case. Thus, two kinds of reservoir-filling injections are necessary, which risks confusing the reservoirs, which may have fatal consequences. Also, the requirement of filtering the urine necessitates exchange of the filter, which requires surgical intervention. Additionally, the detection of sugar content in urine is not a satisfactory manner of detecting the sugar content of blood because, by the time sugar is in the urine, the sugar level is already far too high in the patient's blood. The device may keep the blood sugar under control, therefore, but this will be at far too high a level. Besides, the operation of the device is by battery.

The last-mentioned patent discloses an implantable pump which is, primarily, intended for use in connection with heart diseases by detecting changes in blood pressure, electric signals, and chemical changes in the body. Apart from the sensor detecting changes of blood pressure, there is no disclosure of how the remaining parameters are to be detected. It is only stated that they can be detected. The operation of this device, like that of the above mentioned devices, is also by battery, specifically, the kind known for pacemakers.

It is an object of this invention to remedy some of these disadvantages of the above-described pumps, which means that the following requirements should be fulfilled:

1. The artificial "pancreas" (in the following called gland) should be provided with a reservoir that is filled with insulin by piercing, with a syringe, the skin and a membrane that covers the insulin-containing reservoir of the gland;

2. Said reservoir should be provided with a bleeding unit for injecting insulin into the human body, said unit "sensing" the demand of the body for insulin at any time;

3. Said gland should be 100% reliable and independent of any special sources of energy for operation; and 4. A safety means should close in case of any conceivable fault.

Thus, the invention is an artificial gland for implantation in a human body having a medicament reservoir fillable with a liquid medicament from a syringe. The reservoir is connected by a passage with a casing. A wall of the casing completely or partly comprises a semipermeable membrane for causing changes of pressure inside the casing by osmosis for correspondingly bleeding off, i.e. discharging, some of the medicament.

In a preferred embodiment, the reservoir is connected, via a passage and a one-way valve, with a sponge-like body in the casing for absorbing the medicament. The sponge-like body only occupies part of the space within the casing, and is limited from the remaining, void portion of the space within the casing by a tight film from which channels provided with one-way valves extend outwards, said casing wall consisting of or comprising a semipermeable membrane, and the space between said casing wall and said tight film being filled with tissue fluid when said gland is in use.

In one embodiment of the invention said casing wall consists of a rigid semipermeable membrane permitting an osmotic pressure to build up in the tissue fluid in the space between said casing wall and tight film to force liquid medicament out of said sponge shaped body.

In another embodiment part of said casing wall consists of a resilient semipermeable membrane provided with a pressure means which will urge against said sponge to liberate medicament from said sponge shaped body when said membrane yields in case of a decrease of the osmotic pressure in the tissue fluid in the space between said casing wall and tight film.

In a further embodiment the casing wall consists of a rigid semipermeable membrane connected with a capillary tube leading from said reservoir, a flexible hose extends from the end of said capillary tube that is inside said casing to the opposite casing wall, inside said flexible hose a piston is provided and comprises a central bore leading out through said casing wall, and at its other end opening into a transversal bore which leads out through the exterior piston surface that is covered by said flexible hose.

In a further embodiment a rigid casing is provided with a casing wall that is perforated with small openings and at its front end consists of a rigid semipermeable membrane connected with the capillary tube leading to said reservoir. At the transition zone between said casing wall and membrane a resilient balloon is secured and is in sealing contact with said perforated casing wall by the aid of tension from a sponge that is provided inside said balloon.

The invention is now to be disclosed in detail with reference to the drawings, in which:

FIG. 1 is a schematic cross section of an embodiment, together with a reservoir, syringe and portion of a human body with which it is used;

FIG. 2 is an enlarged cross section of a membrane portion of another embodiment;

FIG. 3 is an enlarged cross section of a membrane portion of still another embodiment; and FIG. 4 is an enlarged cross section of the embodiment of FIG. 1.

FIG. 1 shows the main elements of the gland, together with a syringe "a" and skin b of a human body (not otherwise shown on the left of FIG. 1). The Syringe fills a reservoir d through the skin b and a membrane c. Said reservoir is, via a hose or capillary g, connected with a semipermeable membrane casing e. A check valve h is provided in hose g. Furthermore, a mechanical safety means k, as mentioned under point 4 above, is provided. It functions to close the liquid flow through hose g in case of any physical pressure on reservoir d. Hose g is dimensioned with an opening that is so small that even if safety means k should fail, the friction of the liquid flow in case of pressure on reservoir d will brake the liquid flow to prevent excessive liquid flow to casing e.

The reservoir d is arranged to expand when insulin is supplied to it and collapses when it is emptied. Said collapse is used to emit a mechanical signal indicating an empty reservoir.

Membrane e may be designed in three, for example, different manners:

It may be a polymer (not shown) having pore openings corresponding in size to the glucose (sugar) molecules, which are considerably smaller than insulin molecules.

As shown in FIG. 2 said membrane is a polymer having pore openings with outward facing lips only permitting liquid flow in one direction.

In FIG. 3, said membrane is a polymer with an encased enzyme/substance 2 which reacts by expansion when contacted with glucose and corresponding contraction when the glucose disappears.

FIG. 4 shows an embodiment comprising a non-compressible, semipermeable casing Q forming a chamber space F about one end of a capillary tube passage R from a reservoir (not shown). A flexible hose S extends about the end of the capillary tube inside the casing Q. Inside hose S is also a rod T with a bore U to outside the casing and a bore V transversely communicating with the bore U inside the casing and hose. In case of fluid migration from chamber F due to an increase of the glucose content in the tissue fluid about the casing Q, hose S will bulge out, as shown in phantom, permit insulin delivery from the capillary tube R, along the hose and through bores V and U to outside the casing, as shown by the arrow. In case of a reduction of the glucose content, the opposite will occur, i.e. the hose will return to being about the capillary tube and rod, where it blocks this. No check valve is necessary in this case, therefore.

It applies to all embodiments that the indicator means, i.e. the membrane, is positioned in a place low in pressure in the human body. If this is in the abdominal cavity, it will be achieved at the same time that the insulin essentially will migrate through the liver in the same manner as insulin delivered by the pancreas in healthy people. This will enhance the controlling effect of the gland, because in this case it is to be expected that the so called late complications will be further reduced. Its positioning and the fact that tissue fluid to be formed around the membrane will prevent it from being subjected to exterior pressure causing uncontrolled amounts of insulin to flow out into the body. But even if this could happen in quite extraordinary cases, e.g. in case of a hard blow, only a small amount of insulin will be released and may be compensated, e.g. by intake of sugar, because even pressure cannot influence the membrane as it is not compressible.

Nor should there be any hazard of pressure being exercised on the reservoir due to movement of muscles since fluid flow will be prevented by the safety means k and the capillary hole in hose g, or otherwise by the flexibility between said reservoir and muscle tissue.

Injection of the medicament according to the invention will occur in a manner analogous to the body functions, i.e. a signal is emitted to the gland in question to supply the body with medicament. In the disclosed case the gland is a pancreas and the medicament is insulin.

Besides using the gland for insulin injections as mentioned, it is also possible to use it for injections of all kinds of liquid medication that is dependent on certain changes in the blood composition, e.g. the content of cholesterol.

Another advantage of the invention is that it is not necessary to penetrate a vein in order to detect the glucose content. A foreign body in the blood-stream would be far more subjected to be clogged by proteine, and the like.

Having described my invention, I claim:

1. An artificial gland for implantation into a human body together with a reservoir for filling with a medicant solution with a syringe, the gland comprising:
   a capillary tube for connection to the reservoir, a casing having a wall which is at least partly comprised of a semipermeable membrane for causing changes of pressure inside the casing by osmosis when the casing is implanted in a human body for delivery thereto of the medicant solution of the reservoir, the semipermeable membrane being rigid and the casing being provided in connection with the capillary tube, a flexible hose extending from an end of the capillary tube inside the casing to an opposite portion of the casing wall, the flexible hose being provided with a rod having a center bore that leads out through the opposite portion of the casing wall at one end and opening at its opposite end into a transversal bore leading to an exterior surface of the rod which is covered by the flexible hose.

2. An artificial gland, comprising:

a capillary tube for a passage from a reservoir;

a non-compressible, semipermeable casing forming a chamber about one end of the capillary tube;

a flexible hose about the one end of the capillary tube and inside the casing;

a rod inside the hose, the rod having a first bore to outside the casing and a second bore communicating with the first bore and inside of the hose, whereby fluid migration from the chamber by osmosis through the semipermeable casing bulges the hose from the one end of the capillary tube and the second bore of the rod for fluid flow through the capillary tube and bores from the reservoir to the outside of the casing.

* * * * *